United States Patent [19]

Weber

[11] Plant 4,647

[45] Feb. 10, 1981

[54] CHRYSANTHEMUM PLANT

[75] Inventor: Gordon N. Weber, Milwaukie, Oreg.

[73] Assignee: Weber's Riverside Greenhouses, Milwaukie, Oreg.

[21] Appl. No.: 66,427

[22] Filed: Aug. 14, 1979

[51] Int. Cl.[3] ..... A01H 5/00

[52] U.S. Cl. ..... Plt./78

[58] Field of Search ..... Plt./78–79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant with flat spider capitulum which is a sport of the cultivar Orange Bowl, being distinguished from the parent cultivar by its spider type and medium bronze ray floret color.

1 Drawing Figure

The present invention comprises a new and distinct cultivar of *Chrysanthemum morifolium,* Ramat., hereinafter referred to by the cultivar name of Bolero.

Bolero is a spontaneous mutation of the unpatented cultivar Orange Bowl and was selected to expand the range of capitulum type of the parental variety.

Bolero was discovered and selected by Gordon Neil Weber on June 29, 1976 as one plant within a flowering block of Orange Bowl in Milwaukie, Oreg. The first act of asexual reproduction of Bolero was accomplished on Sept. 8, 1976 when vegetative cuttings were taken from the initial selection in Milwaukie, Oreg. by Gordon Neil Weber.

Continued asexual reproduction by vegetative cuttings for evaluative flowering trials in conjunction with horticultural examination of selected units initiated Feb. 1, 1978 has demonstrated that the combination of characteristics as herein disclosed for Bolero are firmly fixed and are retained through successive generations of asexual reproduction.

Bolero has not been observed under all possible environmental conditions. The phenotype may vary significantly with variations in environment such as temperature, light intensity and daylength. The following observations, measurements and comparisons describe plants grown in Milwaukie, Oreg. and Salinas, Calif. under environmental conditions which approximate those generally used in commercial practice.

The following traits have been repeatedly observed and are determined to be basic characteristics of Bolero which in combination distinguish this chrysanthemum as a new and distinct cultivar:

(1) spider capitulum type;

(2) flat capitulum form;

(3) medium bronze ray floret color;

(4) diameter across face of inflorescence ranging from 125 to 150 mm. at maturity;

(5) uniform ten week photoperiodic flowering response to short days;

(6) medium plant height (requiring 1–2 long day weeks prior to pinch and short days, and 1 application 2500 ppm B-9 SP 14 to 21 days after pinch to attain a flowered plant height of 30 to 35 cm. when grown as a pinched disbudded pot plant for April through November flowerings in Salinas, Calif.); and (7) spreading branching pattern.

The accompanying color photographic drawing shows typical inflorescence and foliage characteristics of Bolero, with colors being as true as possible with photographs of this type.

The photographic drawing depicts typical summer ray floret color of Bolero. During flowering periods of cooler temperatures the ray floret color of Bolero becomes more intense in coloration.

Of the many commercial cultivars known to the present inventors, the most similar in comparison to Bolero is Orange Bowl. Reference is made to attached Chart A which compares certain characteristics of Bolero with the same characteristics of Orange Bowl. In general comparison to Orange Bowl, Bolero has different capitulum type, different capitulum form, and different ray floret color. Other characteristics of Bolero are similar to those same characteristics of Orange Bowl.

In the following description, color references are made to A Limit Color Cascade, published by the Munsell Company, 1972 edition. The color values were determined between 10:00 and 10:30 a.m. on June 1, 1979 under 100 foot-candle light intensity at Salinas, Calif.

Classification:

*Botanical.*—*Chrysanthemum morifolium,* Ramat., cv Bolero.

*Commercial.*—Pinched or single stem disbudded pot plant.

I. Inflorescence:

A. *Capitulum.*—Form: Flat. Type: Spider. Permanence: 14 to 18 days. Diameter Across Face: 90 to 115 mm.

B. *Corolla of ray florets.*—Color (general tonality): Orange bronze (29-11 streaked over 27-5). Color (abaxial): 29-11 streaked heavily over 27-7 (immature) oxidizing to 29-11 streaked lightly over 27-7. Color (adaxial): 29-11 streaked lightly over 27-5.

C. *Reproductive organs.*—Androecium: Absent. Gynoecium: Present in ray florets.

II. Plant:

A. *General appearance.*—Branching Pattern: Spreading. Height: Medium (pot mum culture).

B. *Foliage.*—Color (abaxial): Approximately 22-14. Color (adaxial): Approximately 22-14 overlaid with white.

CHART A
COMPARISON OF BOLERO
AND ORANGE BOWL

| CULTIVAR | RAY FLORET COLOR | DIAMETER ACROSS FACE OF CAPITULUM | PLANT HEIGHT |
|---|---|---|---|
| Bolero | Medium Bronze | 125 to 150 mm. | Medium |
| Orange Bowl | Orange Bronze | 125 to 150 mm. | Medium |

| CULTIVAR | BRANCHING PATTERN | FLOWERING RESPONSE PERIOD | CAPITULUM FORM AND TYPE |
|---|---|---|---|
| Bolero | Spreading | 10 week | Flat Spider |

-continued

CHART A
COMPARISON OF BOLERO
AND ORANGE BOWL

| | | | |
|---|---|---|---|
| Orange Bowl | Spreading | 10 week | Informal Incurved Decorative |

COMPARISONS MADE OF PLANTS GROWN IN MILWAUKIE, OREGON AND SALINAS, CALIFORNIA AS PINCHED DISBUDDED PLANTS.

I claim:

1. A new and distinct cultivar of *Chrysanthemum morifolium,* Ramat., known by the cultivar name Bolero and particularly characterized as to uniqueness by the combined characteristics of spider capitulum type; flat capitulum form; medium bronze ray floret color; diameter across face of capitulum from 125 to 150 mm. at maturity; uniform ten week flowering response to photoperiodic short-day control; medium plant height and spreading branching pattern.

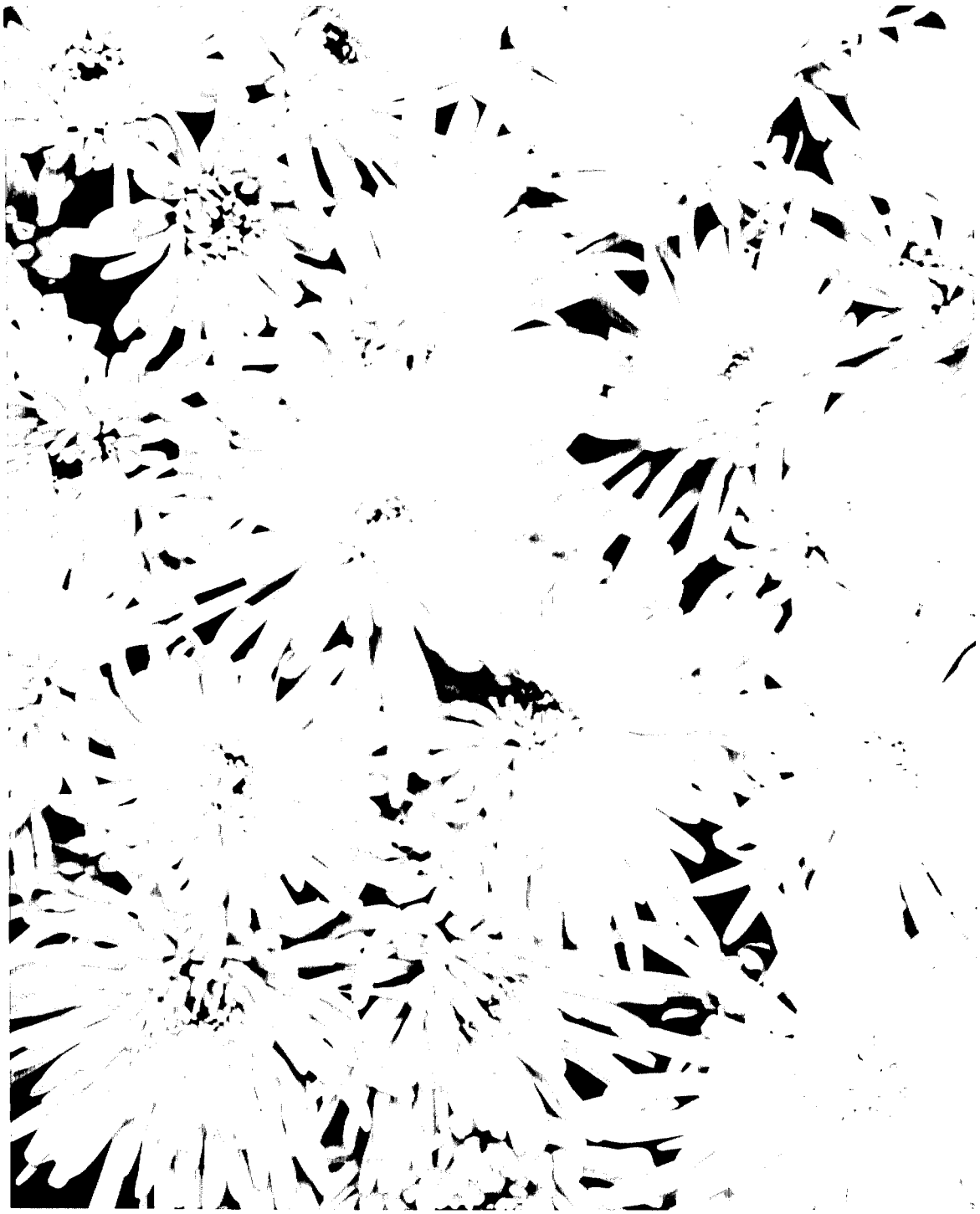

* * * * *